United States Patent [19]

DeLucia

[11] 4,455,462
[45] Jun. 19, 1984

[54] ARC PROOF DUAL INTERLOCK SAFETY SWITCH

[76] Inventor: Victor E. DeLucia, 11846 Mississippi Ave., Los Angeles, Calif. 90025

[21] Appl. No.: 342,520

[22] Filed: Jan. 25, 1982

[51] Int. Cl.³ .............................................. H01H 3/16
[52] U.S. Cl. ................................ 200/61.62; 200/61.7; 200/61.81; 200/61.82; 361/2
[58] Field of Search ............... 361/1, 2; 200/1 V, 1 B, 200/61.62, 61.66, 61.68, 61.8, 61.81, 61.82; 339/256 S, 4

[56] References Cited

U.S. PATENT DOCUMENTS

| | | | |
|---|---|---|---|
| 595,963 | 12/1897 | McCaughey | 200/61.82 |
| 2,305,749 | 12/1942 | Voigt | 200/61.81 |
| 2,437,777 | 3/1948 | Zajc | 200/61.82 X |
| 3,147,468 | 9/1964 | Daniels | 200/61.68 X |
| 3,627,959 | 12/1971 | Chapell | 200/61.62 |
| 3,659,063 | 4/1972 | Peterson | 200/61.7 |
| 3,729,603 | 4/1973 | Foltz | 200/61.7 |
| 3,984,733 | 10/1976 | DeLucia | 361/2 |

Primary Examiner—J. R. Scott
Attorney, Agent, or Firm—Keith D. Beecher

[57] ABSTRACT

A dual interlock switch assembly is provided which has particular although not exclusive application to X-ray units to prevent the unit from being energized whenever the access door is opened. The assembly includes a plug, formed of insulating material such as epoxy glass, mounted on the access door, and a tubular socket mounted on the cabinet which receives the plug when the door is closed. The plug has two mutually separated conductive segments bonded to its end, and one of the segments initially interconnects a first pair of spring-loaded conductive pins mounted in the socket, and the other segment subsequently interconnects a second pair of spring-loaded conductive pins mounted in the tubular socket as the door is closed, with the process being repeated in reverse when the door is opened. The conductive pins are connected into the circuitry of the X-ray unit in a manner such that the unit is de-energized when the door is opened and energized when the door is closed without arcing.

4 Claims, 3 Drawing Figures

4,455,462

ARC PROOF DUAL INTERLOCK SAFETY SWITCH

BACKGROUND

U.S. Pat. No. 3,984,733 which issued in the name of the present inventor discloses an arc proof dual interlock safety switch which is intended to fulfill the same purpose as the switch assembly of the present invention. The interlock switch described in the patent includes two microswitches connected in series, and which are actuated when the access door is closed, this being accomplished by a pair of contact posts mounted on the door which move against a pair of spaced electrically conductive strips, initially to interconnect the strips, and then to move the strips against the actuator buttons of the microswitches. The resulting switch assembly provides electrical switching without arcing when the door is opened or closed.

The assembly of the present invention has certain advantages over the switch described in the patent in that it accomplishes its intended purpose in a simpler and more straight-forward manner. The use of a plug in the place of the contact posts is advantageous in that the posts had a tendency to break, whereas the plug is strong and rigid. Moreover, the plug is capable of more efficient linear travel than the posts, and it applies a more positive force to the electric contacts in the socket. Moreover, the assembly of the present invention obviates the need for the relatively expensive microswitches used in the switch described in the patent.

The interlock switch assembly of the present invention, as is the case with the assembly described in the patent, is constructed principally for use in X-ray systems in order to protect the health and safety of the personnel operating the systems. However, it will become evident as the description proceeds that the switch assemblies have general application for providing an effective electrical interlock which operates in conjunction with access doors, and which positively prevents the application of electric power to equipment when such access doors are open, even in the event of failure of the power relays in the electrical system.

Many types of interlock systems have been used in the past, and even with such prior art systems medical and industrial accidents have occurred because the interlock systems failed, subjecting the operators to exposure of X-rays. An important feature of the interlock assembly of the present invention, as is the case with the assembly of the patent, is that it assures that the power is cut off from the X-ray machine when the access door is opened, regardless of any faults that may have occurred in the energizing circuit. The circuitry associated with the interlock switch assembly of the invention is such that power can be applied to the X-ray unit only when the door is closed, at which time the circuits are closed mechanically and electrically, and only then can the unit be activated. Arcing is prevented in the use of the interlock switch of the invention, since the switch serves to open the circuit to the power control relay in the energizing circuit to de-energize that relay prior to the physical breaking of contact with the power source itself.

DETAILED DESCRIPTION OF THE ILLUSTRATED EMBODIMENT

Figure 1:
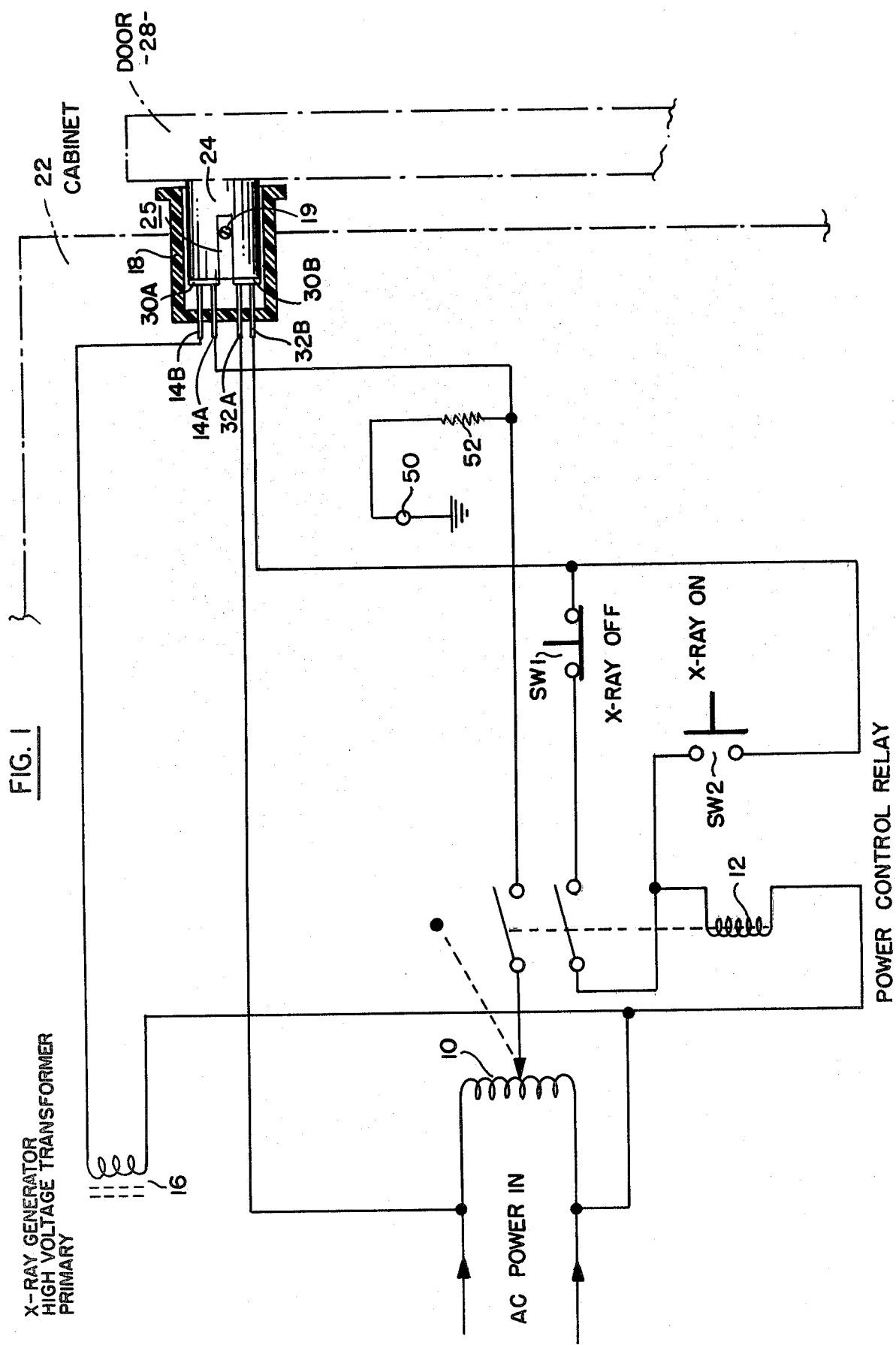
FIG. 1 is a schematic diagram showing the components of the safety interlock switch assembly of the invention, and also showing an X-ray generator energizing circuit in which the assembly may be incorporated.

In the system of FIG. 1, alternating current power at the usual source voltage (115 volts AC) is applied to a variable voltage transformer 10, which constitutes a high voltage control for the X-ray generator. One side of transformer 10 is connected through a pair of normally open contacts of a power control relay 12 to one of the spring-loaded contacts 14A which is mounted in a tubular socket 18 and which constitute a part of the interlock switch of the invention. The tubular socket 18, as shown, is mounted in the wall of a cabinet 22, and a plug 24 is received in the socket when the access door 28 of the unit is closed. As also illustrated, plug 24 has a first conductive segment 30A clad to its end, and this segment bridges the contact pin 14A and a further spring-loaded contact pin 14B as the plug 24 is received in the socket. The plug 24 also has a second segment 30B of conductive material clad to its end, and this second segment bridges a pair of spring-loaded contact pins 32A and 32B when the plug is received in the socket. The plug has a slot 25 between the two conductive segments, as shown. A pin 19 of insulating material is mounted in socket 18 for guiding purposes and to prevent anyone from inserting their fingers in the socket. The pin is received in the slot 25 when the plug is inserted into the socket.

The plug may be formed, for example, of epoxy glass, and the conductive segments 30A and 30B may be composed of copper, or other appropriate conductive material, and are clad to the end of plug 24 by known techniques used, for example, in the construction of printed circuits.

The assembly is such that the spring-loaded pins 14A and 14B extend into socket 18 a distance greater than the spring-loaded pins 32A and 32B. This means that when plug 24 is recieved in the socket, when door 28 is closed, the pins 14A and 14B are contacted first, and the pins 32A and 32B are contacted subsequently. Also, when the door is opened, the pins 32A and 32B are disconnected first, and then the pins 14A and 14B are subsequently disconnected.

The other side of transformer 10 is connected to one side of the primary winding of the usual high voltage X-ray generator transformer 16, and the high voltage X-ray tube is energized through a circuit (not shown) connected to the secondary of transformer 16.

The other side of the variable voltage transformer 10 is connected to the energizing coil of the power control relay 12, and the other side of the energizing coil is connected through a pair of normally open holding contacts of the relay and through a pushbutton stop switch SW1 to contact pin 32B of the switch assembly of the invention. The other side of the energizing winding of relay 12 is also connected through a pushbutton start switch SW2 to the contact pin 32B. Contact pin 32A is connected back to the other side of the variable voltage transformer 10.

During normal operation of the system, door 28 is closed, so that the system assumes the operating condition shown in FIG. 1, in which the contact pins 32A and 32B are interconnected by the segment 30B on plug 24; and the contact pins 14A and 14B are interconnected by the segment 30A on the plug. Now the switch SW2 may be momentarily operated to energize power relay 12 to cause the relay to close its contacts and energize the unit, the relay being held energized by its holding contacts described above. Power is now supplied to the primary of transformer 16 through the relay contacts, and across the contacts 14A and 14B of the interlock switch.

The high voltage of the generator may then be controlled, in usual manner, by manual control of the variable voltage transformer 10, until the meter on the control panel of the unit (not shown) indicates that the required high voltage has been achieved. The holding contacts of the power relay 12 maintain the power relay energized under these conditions, through the normally closed switch SW1 and through the holding contacts of the relay, even though switch SW2 has been released. To terminate the operation, pushbutton switch SW1 is operated to break the holding circuit, and to cause the power control relay 12 to become de-energized. The relay contacts then open breaking the circuit to the primary of transformer 16.

An indicator lamp 50 may be provided, and this lamp is connected through a ballast resistor 52 to contact pin 14A, and has its other contact grounded. This indicator lamp is energized whenever the power control relay contacts are closed. The lamp is mounted in a position to be observed on the control panel whenever the access door is opened. Under normal conditions, the lamp should turn off when the access door is opened, since the power control relay is normally de-energized when the door is opened. However, should the power control relay fail in a closed condition, the lamp 50 will remain on, indicating the failed condition to the operator.

Under normal conditions, should door 28 be opened while the system is energized, the contacts 32A and 32B will open first, breaking the connection to the power control relay, so that the power control relay will become de-energized, opening its relay contacts and breaking the circuit to transformer 16. Thereafter, as the door is opened further, the contacts 14A and 14B will open, but no arcing will occur since the circuit will have already been broken by the microswitches. In the event that the power relay fails in its on condition, the circuit to the primary of transformer 16 will still be opened, due to the fact that the connection across the contact pins 14A and 14B is broken as the door opens, although under such failed conditions, arcing will occur.

In closing the door, contact is first made across the contact pins 14A and 14B in the circuit of the primary of transformer 16, and then contact is made across the contact pins 32A and 32B in the circuit of the power control relay. Only then may the system be energized by momentarily depressing the switch SW2. It should be stressed that under no conditions can the circuit become energized if the door is opened, even though relay 12 may fail in a closed condition. The open circuit is assured because of the open condition of the contact pins 14A and 14B.

As mentioned above, should the power control relay 12 fail within its contacts welded into a closed condition, the contacts 32A and 32B are no longer capable of opening the circuit, since even though the power control relay is de-energized its contacts remain closed, and transformer 16 remains energized. However, under such conditions, when the door is opened, and as also explained above, plug 24 physically breaks contact with the contact pins 14A and 14B to break the circuit to the primary of transformer 16. Indicator lamp 50 will now glow, even though the door is opened, apprising the operator of the failed condition.

Figure 2:
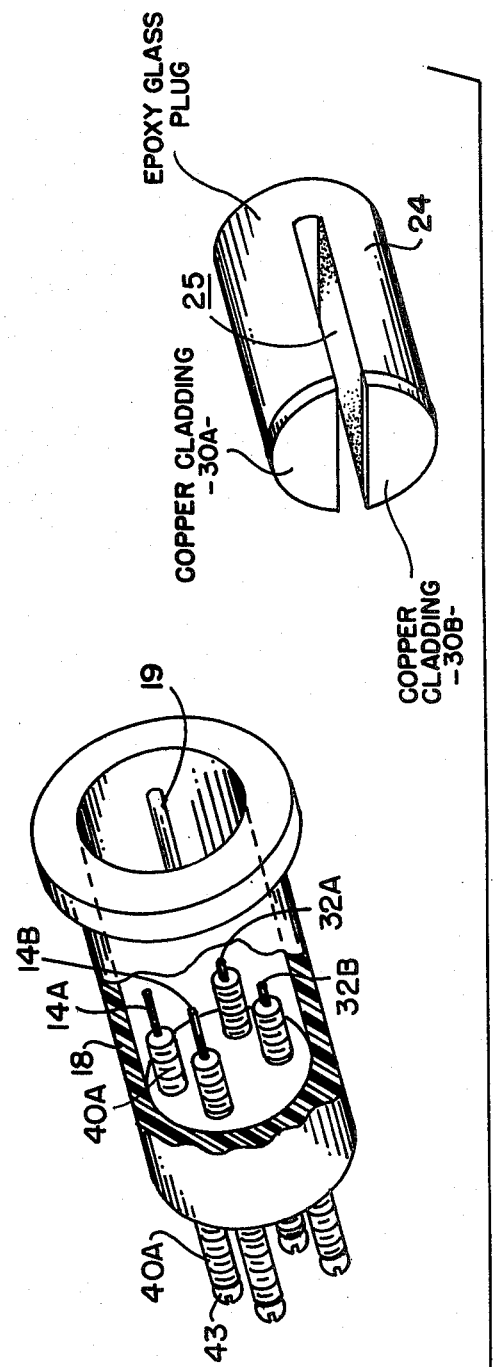
FIG. 2 is a perspective representation of the switch assembly of FIG. 1.
Figure 3:
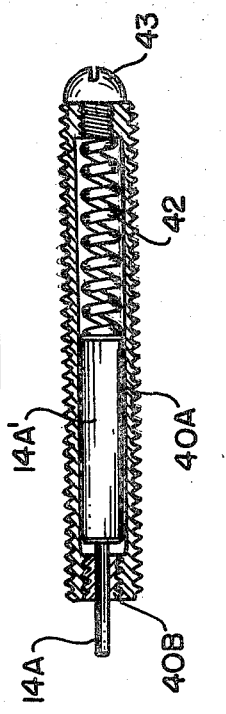
FIG. 3 is a sectional representation of one of the spring-loaded pins included in the switch assembly, the assembly including four such pins.

FIG. 2 shows the details of plug 24 and tubular socket 18, and FIG. 3 shows the details of spring-loaded contact pin 14A, it being understood that the other contact pins 14B, 32A and 32B are similarly constructed.

As shown in FIG. 3, spring-loaded pin 14A is received in a bushing 40A, and it extends through a second bushing 40B which is threaded into one end of bushing 40A. The pin 14A has an enlarged end portion 14A' which defines a shoulder at its forward end. A coil spring 42 engages the end of portion 14A' of pin 14A and biases the pin to the left in FIG. 3 until the annular shoulder engages the inner end of bushing 40A. Bushing 40A is threaded into the end of socket 18. A connecting screw 43 is threaded into the end of bushing 40A. The enlarged portion 14A' of pin 14A maintains good sliding electric contact with the inner surface of bushing 40A.

The invention provides, therefore, an improved and simplified interlock safety switch assembly which is rugged in its construction and not subject to breakage, and which provides absolute assurance that under no conditions will an operator of an X-ray unit, or the like, be susceptible to harmful radiation by opening the access door, since the safety interlock switch assembly of the invention provides absolute assurance that the energizing circuit will be de-energized when the door is opened.

It will be appreciated that although a particular embodiment of the invention has been shown and described, modifications may be made. It is intended in the claims to cover the modifications which come within the spirit and scope of the invention.

What is claimed is:

1. A dual interlock switch assembly for use in a circuit connecting a source of electrical energy to the energizing circuit of an X-ray unit, and the like, which unit includes a cabinet and an access door and in which the switching circuit serves to prevent energization of the unit when the access door is open, the assembly including: a socket mounted on the cabinet having a closed end and an open end; a first pair of electric contacts mounted in the socket each in the form of a spring-loaded pin extending through the closed end longitudinally into the socket; a second pair of electric contacts mounted in the socket each in the form of a spring-loaded pin extending longitudinally through the closed end; a plug mounted on the access door removably received in the open end of the socket and engaging the spring-loaded pins to interconnect said first pair of contacts and subsequently to interconnect said second pair of contacts as the door is closed, and disengaging with said pins to break contact with said second pair of contacts and subsequently to break contact with said first pair of contacts as the door is opened.

2. The circuit defined in claim 1, in which the spring-loaded pins of the first pair of contacts extend longitudinally into the socket further than the spring-loaded pins of the second pair.

3. The circuit defined in claim 1, in which the plug is formed of electrical insulating material, and which includes a pair of mutually insulated electrically conductive segments mounted at the end of the plug respectively to interconnect the pins of the first pair of electric contacts and the pins of the second pair of electric contacts as the door is closed.

4. The circuit defined in claim 3, in which the plug has a slot therein between the electrically conductive segments, and which includes a pin mounted in said socket and extending transversely thereacross to be received in the slot.

* * * * *